United States Patent
Hsieh et al.

(10) Patent No.: US 8,816,134 B2
(45) Date of Patent: Aug. 26, 2014

(54) METHOD FOR MAKING DIMETHYL ETHER BY REACTIVE-DISTILLATION

(75) Inventors: Cheng-Ting Hsieh, Taichung (TW); How-Ming Lee, Taoyuan County (TW); Kuo-Chao Liang, Chiayi County (TW); Chin-Ching Tzeng, Taipei County (TW)

(73) Assignee: Institute of Nuclear Energy Research, Atomic Energy Council, Lungtan, Taoyuan (TW)

( * ) Notice: Subject to any disclaimer, the term of this patent is extended or adjusted under 35 U.S.C. 154(b) by 513 days.

(21) Appl. No.: 13/044,271

(22) Filed: Mar. 9, 2011

(65) Prior Publication Data
US 2012/0232311 A1    Sep. 13, 2012

(51) Int. Cl.
*C07C 41/09*    (2006.01)
*C07C 43/04*    (2006.01)
*B01D 3/00*    (2006.01)

(52) U.S. Cl.
CPC .............. *B01D 3/009* (2013.01); *C07C 41/09* (2013.01)
USPC ........................................................... 568/698

(58) Field of Classification Search
CPC ................................. C07C 41/09; C07C 41/42
USPC ........................................................... 568/698
See application file for complete search history.

(56) References Cited

U.S. PATENT DOCUMENTS

| | | | |
|---|---|---|---|
| 5,057,468 A * | 10/1991 | Adams | 502/1 |
| 2007/0066855 A1 | 3/2007 | Malandrino et al. | |
| 2009/0048468 A1 | 2/2009 | Varkiani et al. | |
| 2009/0069607 A1 | 3/2009 | Smith, Jr. et al. | |

FOREIGN PATENT DOCUMENTS

CN    1907932 B  *  8/2005  .............. C07C 43/04

* cited by examiner

*Primary Examiner* — Rosalynd Keys
(74) *Attorney, Agent, or Firm* — Jackson IPG PLLC

(57) ABSTRACT

Disclosed is a method for making dimethyl ether by reactive distillation. The method provides a reactive distillation tower with a top, a bottom, and rectification, reaction and stripping zones defined therein. The top of the reactive distillation tower is retained at 25° C. to 40° C. while the bottom of the reactive distillation tower is retained at 84.6° C. to 170° C. Each of the rectification, reaction and stripping zones includes several sieving trays. The reaction zone of the reactive distillation tower is filled with catalyst. The pressure in the reactive distillation tower is lower than 8.0 bars. Methanol is introduced into the reactive distillation tower so that the methanol travels from the reaction zone toward the bottom for contact with the catalyst to provide a top stream and a bottom stream. The top stream includes dimethyl ether. The bottom stream includes water and a remaining portion of the methanol. Finally, the dimethyl ether is collected in the top of the reactive distillation tower. The purity of the collected dimethyl ether is higher than 99%.

11 Claims, 3 Drawing Sheets

METHOD FOR MAKING DIMETHYL ETHER BY REACTIVE-DISTILLATION

BACKGROUND OF THE PRESENT DISCLOSURE

1. Technical Field

The present disclosure relates to a method for making dimethyl ether by reactive-distillation and, more particularly, to a method for making dimethyl ether by a reactive-distillation tower, a combination of a reactor with a distillation tower.

2. Related Prior Art

The boiling point of dimethyl ether ("DME", $CH_3OCH_3$) is $-25°$ C. at the atmospheric pressure. At the normal temperature, dimethyl ether can be pressurized at 5.4 bars and liquidized for convenience in storage, transportation and use. Dimethyl ether is often used for spray. As shown by statistics, about 500 million tons of dimethyl ether was made around the world in the year of 2009. The production of dimethyl ether is of considerable commercial value. Because the natures of dimethyl ether are like that of liquidated petroleum gas, dimethyl ether can be added into liquidated petroleum gas for replacement. Hence, dimethyl ether is deemed a new energy carrier in the $21^{st}$ century. Furthermore, the combustion of dimethyl ether is cleaner than that of diesel. Hence, dimethyl ether is more environmentally friendly than fossil fuel.

Dimethyl ether is commercially made by dehydrating methanol all over the world. In a commercial process, there are two devices used, i.e., a reactor and a dimethyl ether separation and purification device. The dimethyl ether separation and purification device is a distillation tower or packing tower in most cases. Methanol is dehydrated in the reactor to provide dimethyl ether and water. The dimethyl ether is collected from a stream produced after the reaction and purified in the dimethyl ether separation and purification device. Because the dehydration is limited by chemical equilibrium, the conversion ratio of the methanol to the dimethyl ether is 80% to 90%. That means, about 20% to 10% of the methanol is wasted, or another separation and purification device must be used to recycle and purify the methanol.

Moreover, as the process for making dimethyl ether by dehydrating methanol is an exothermal reaction, it is conventionally difficult to reuse the heat released from the dehydration. This is a waste of energy.

Reactive distillation has been devised to overcome the foregoing problems. The reactive distillation is based on chemical equilibrium and Le Chatelier's principle. For chemical reactions that are limited by chemical equilibrium, reactants are instantly separated from products. A product with a higher relative volatility is separated from a reactant with a lower relative volatility in a distillation tower. The product with the higher relative volatility is removed from the distillation tower to facilitate further production of the product and reduce risks of side reactions. Therefore, reactive distillation is commercially beneficial.

Reactive distillation processes can be found in US 2007/0066855 A1, US 2009/0048468 A1 and US 2009/0069607 A1 for example. The pressure in a reactive distillation tower must be higher than 8 bars to make dimethyl ether by dehydrating methanol as disclosed in these documents. However, the higher the pressure is, the higher the cost is in constructing and operating the equipment and in consuming energy.

Moreover, in Stanislao et al., 2007, the pressure of the reactive distillation tower must be 8 to 12 bars to make dimethyl ether by dehydrating methanol. The cost is also high in constructing and operating the equipment and in consuming energy.

The present disclosure is therefore intended to obviate or at least alleviate the problems encountered in prior art.

SUMMARY OF THE PRESENT DISCLOSURE

It is an objective of the present disclosure to provide a method for making dimethyl ether by dehydrating methanol in a single, small and inexpensive piece of equipment.

It is another objective of the present disclosure to provide a method for making dimethyl ether by dehydrating methanol while consuming a reduced amount of energy.

It is another objective of the present disclosure to provide a method for making dimethyl ether by dehydrating methanol while producing a reduced amount of pollution.

To achieve the foregoing objectives, the method includes the step of providing a reactive distillation tower with a top, a bottom, and rectification, reaction and stripping zones defined therein. The top of the reactive distillation tower is retained at $25°$ C. to $40°$ C. while the bottom of the reactive distillation tower is retained at $84.6°$ C. to $170°$ C. Each of the rectification, reaction and stripping zones includes several sieving trays. The reaction zone of the reactive distillation tower is filled with catalyst. The pressure in the reactive distillation tower is lower than 8.0 bars. Methanol is introduced into the reactive distillation tower so that the methanol travels from the reaction zone toward the bottom for contact with the catalyst to provide a top stream and a bottom stream. The top stream includes dimethyl ether. The bottom stream includes water and a remaining portion of the methanol. Finally, the dimethyl ether is collected in the top of the reactive distillation tower. The purity of the collected dimethyl ether is higher than 99%.

Other objectives, advantages and features of the present disclosure will be apparent from the following description referring to the attached drawings.

BRIEF DESCRIPTION OF THE DRAWINGS

The present disclosure will be described via detailed illustration of the preferred embodiment referring to the drawings wherein.

DETAILED DESCRIPTION OF THE PREFERRED EMBODIMENT

Figure 1:
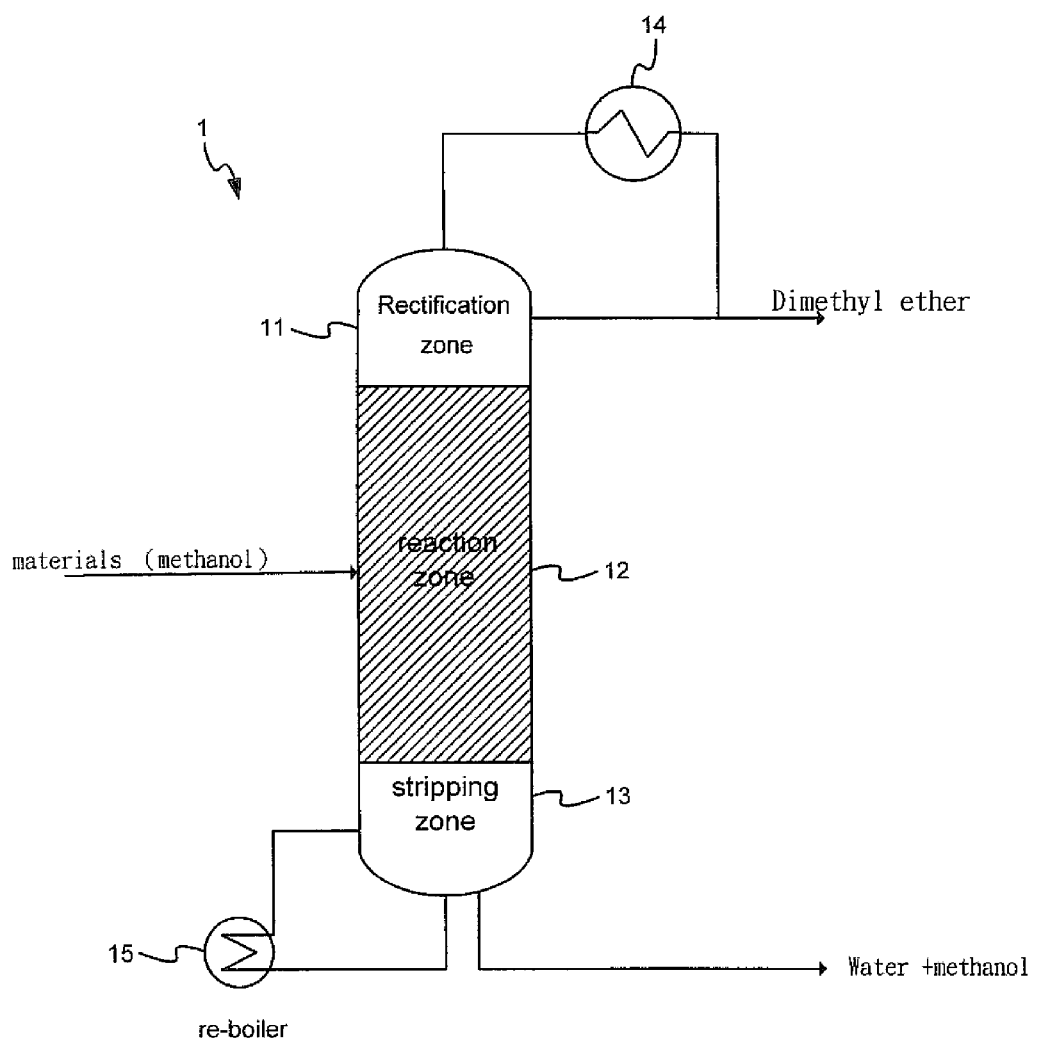
FIG. 1 is a block diagram of a reactive distillation tower used in a method for making dimethyl ether by dehydrating methanol according to the preferred embodiment of the present disclosure.

FIG. 1 shows a reactive distillation tower 1 for use in a method for making dimethyl ether by dehydrating methanol according to the preferred embodiment of the present disclosure. The reactive distillation tower 1 is formed with a top and a bottom. The interior of the reactive distillation tower 1 includes a rectification zone 11, a reaction zone 12 located beneath the reaction zone 12, and a stripping zone 13 located beneath the reaction zone 12. Furthermore, a condenser 14 is connected to the top of the reactive distillation tower 1, and a re-boiler 15 is connected to the bottom of the reactive distillation tower 1.

In the method, the top of the reactive distillation tower 1 is retained at 25° C. to 40° C. while the bottom of the reactive distillation tower 1 is retained at 84.6° C. to 170° C. Catalyst is filled in the reaction zone 12 of the reactive distillation tower 1.

The catalyst filled in the reaction zone 12 of the reactive distillation tower 1 includes at least one dehydrating solid catalyst. The catalyst can be aluminum oxide, silicon oxide, thorium oxide, zirconium oxide, tricalcium phosphate, $ZnAl_2O_4$, $Al_2O_3$—$SiO_2$, $Al_2O_3$—$Cr_2O_3$, $Al_2O_3$—$MgO/SiO_2$, $MgO$—$Al_2O_3$, cadmium oxide, zinc oxide, ZSM-5, a molecular sieve and/or acidic ion exchange resin.

Each of the rectification zone 11, the reaction zone 12 and the stripping zone 13 may include several sieving trays located therein. Alternatively, each of the rectification zone 11, the reaction zone 12 and the stripping zone 13 may include an irregular inert material located therein. The irregular inert material is a rasching ring, a lessing ring or a pall ring.

The pressure in the reactive distillation tower 1 is retained lower than 8.0 bars, and methanol is introduced into the reaction zone 12 of the reactive distillation tower 1. The purity of the methanol is about 90%. The methanol travels from the reaction zone 12 toward the bottom and goes into contact with the catalyst so that the methanol is dehydrated to provide dimethyl ether. Being highly volatile, the dimethyl ether is in the form of gas at the temperature under the pressure. Hence, there is a top stream traveling toward the top of the reactive distillation tower 1. The top stream includes the dimethyl ether. Moreover, there is a bottom stream traveling toward the bottom of the reactive distillation tower 1. The bottom stream includes water and a remaining portion of the methanol.

The re-boiler 15 heats and vaporizes the remaining portion of the methanol in the bottom stream so that it ascends toward the top of the reactive distillation tower 1. The condenser 14 condenses the remaining portion of the methanol so that the remaining portion of the methanol descends and gets in contact with the catalyst. This process is repeated to increase the ratio of the conversion of the methanol to the dimethyl ether.

Finally, the dimethyl ether is collected from the top of the reactive distillation tower 1. The purity of the collected dimethyl ether is high. The purity of the collected dimethyl ether is higher than 99%. Water and a very small portion of the methanol are collected from the bottom of the reactive distillation tower 1.

In practice, 99% of methanol and 1% of water are introduced into the reaction zone 12 of the reactive distillation tower 1 at a rate of 114 ton/hour as shown in FIG. 1. The reactive distillation tower 1 includes 20 distillation theoretical trays, with the condenser 14 as the first tray, the re-boiler 15 as the $20^{th}$ tray, the rectification zone 11 as the second to fourth trays, the reaction zone 12 as the fifth to $15^{th}$ trays, the stripping zone 13 as the $16^{th}$ to $19^{th}$ trays. When the reactive distillation tower 1 is operated at 6 bars, all the condenser 14 needs is water at the room temperature to condense the top stream to become liquid. The dehydration of the methanol is fast, the dehydration of the methanol can reach chemical equilibrium at every tray of the reaction zone 12 of the reactive distillation tower 1. When the methanol is fed into the reactive distillation tower 1 through the $8^{th}$ tray, and the reflux ratio is 0.188, and the ratio of the output of the dimethyl ether from the top of the reactive distillation tower 1 over the input of the methanol into the reactive distillation tower 1 is 0.49, the purity of the dimethyl ether collected from the top of the reactive distillation tower 1 can be as high as 99.5 mole % at 25.6° C. The materials collected from the bottom of the reactive distillation tower 1 includes about 97.6 mole % of water, 2.4 mole % of methanol and a very small amount of dimethyl ether at 154° C. The power of the condenser 14 is −10.9 MW, the power of the re-boiler 15 is 10.4 MW. Thus, the conversion ratio of the methanol can be as high as 98.597%.

Figure 2:
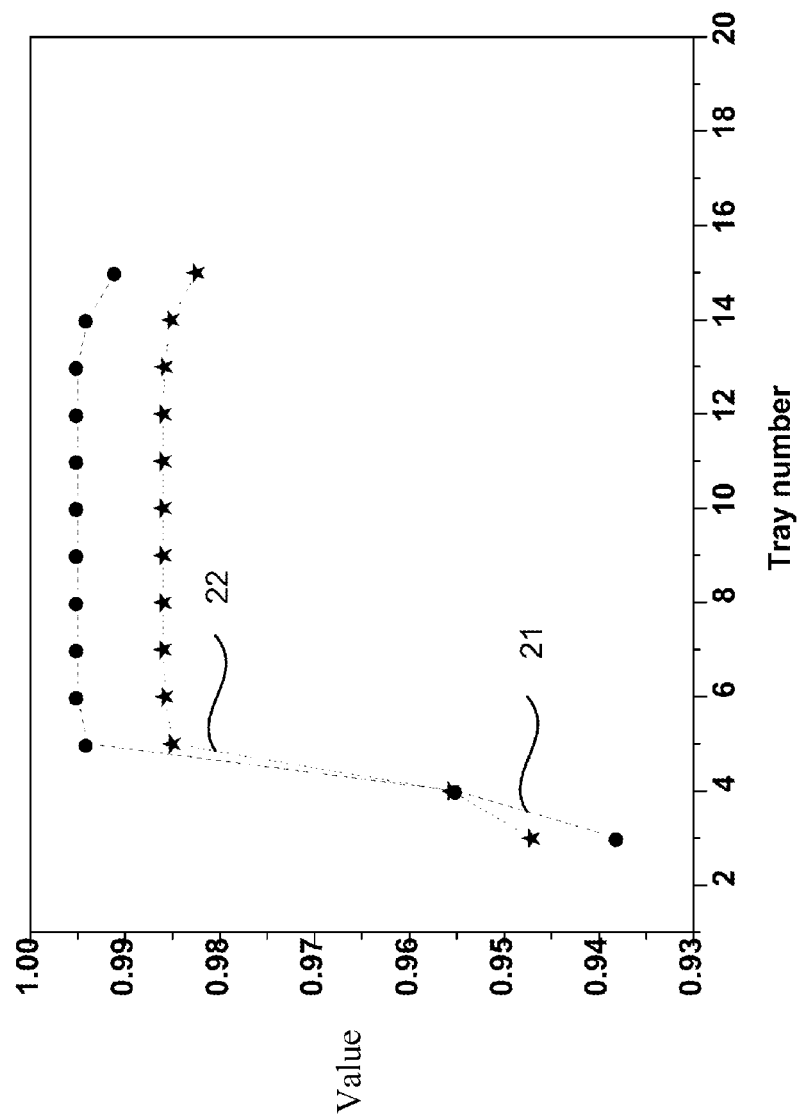
FIG. 2 is a chart of the relationship of a position where the methanol is fed to the conversion ratio of the methanol to the dimethyl ether in the reactive distillation tower shown in FIG. 1.
Figure 3:
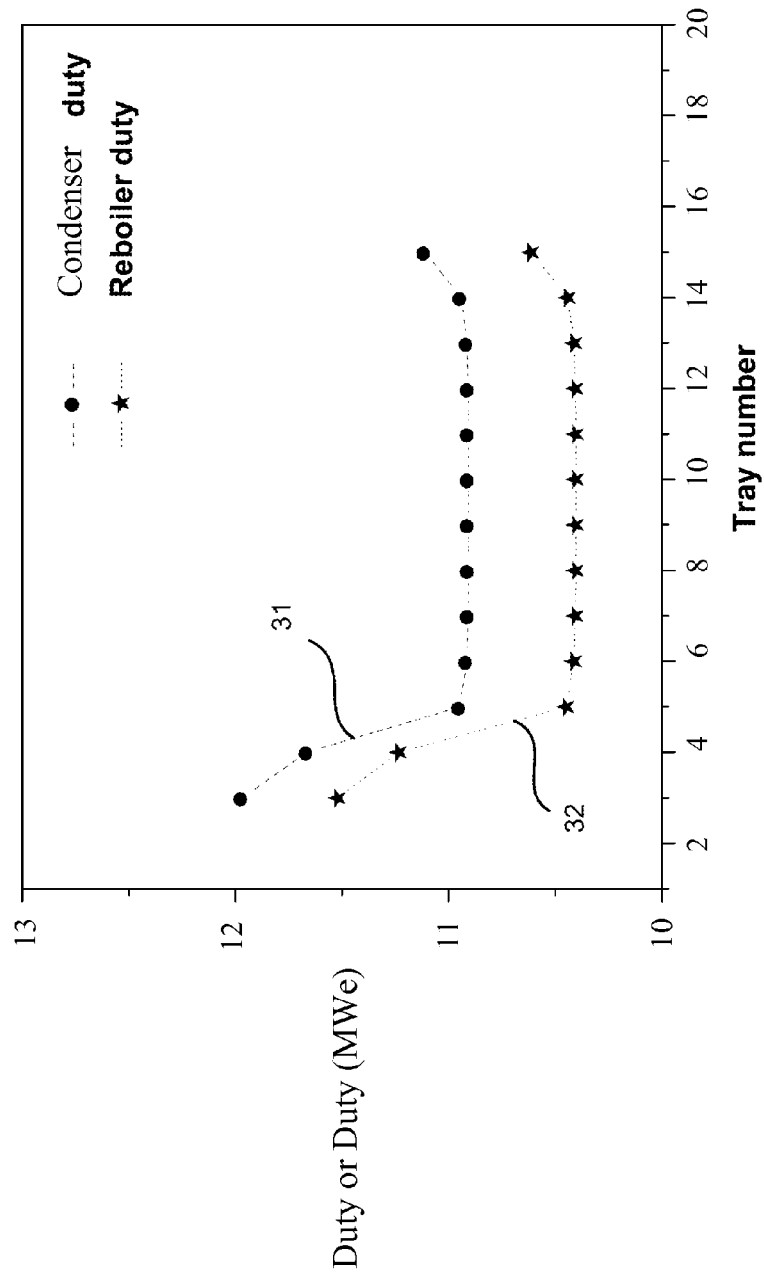
FIG. 3 is a chart of the relationship of the position where the methanol is fed to the power of a condenser and that of a re-boiler in the reactive distillation tower shown in FIG. 1.

FIG. 2 shows the relationship of a position where the methanol is fed to the conversion ratio of the methanol to the dimethyl ether in the reactive distillation tower 1. FIG. 3 shows the relationship of the position where the methanol is fed to the power of a condenser and that of a re-boiler in the reactive distillation tower 1. The position where the methanol is fed to the conversion ratio of the methanol to the dimethyl ether in the reactive distillation tower 1 imposes impacts on the performance of the reactive distillation tower 1 and the consumption of energy. Hence, the reflux ratio and the ratio of the output of the dimethyl ether from the top of the reactive distillation tower 1 over the input of the methanol into the reactive distillation tower 1 are given for illustrating that the conversion ratio of the methanol and the purity of the dimethyl ether collected from the top of the reactive distillation tower 1 change as the feeding position changes.

FIG. 2 shows a dimethyl ether purity curve 21 and a methanol conversion ratio curve 22. As shown in FIG. 2 and Table 1 below, when the methanol is fed into the reactive distillation tower 1 between the $8^{th}$ and $11^{th}$ trays, the purity of the dimethyl ether and the conversion ratio of the methanol are the highest.

FIG. 3 shows a condenser heat duty curve 31 and a re-boiler heat duty curve 32. As shown in FIG. 3 and Table 1, when the methanol is fed into the reactive distillation tower 1 between the $8^{th}$ and $11^{th}$ trays, the amount of heat removed from the denser 14 is littler, and so is the amount of heat supplied by the re-boiler 15. It has been found advantageous to feed the methanol into the reactive distillation tower 1 through the reaction zone 12 regarding the performance of the reactive distillation tower 1 and the consumption of energy.

TABLE 1

| Tray number | Purity | Conversion | Condensor duty (MWe) | ⌈Reboiler duty (MWe)⌉ |
| --- | --- | --- | --- | --- |
| 3 | 93.8 | 94.718 | −11.968 | 11.520 |
| 4 | 95.5 | 95.558 | −11.663 | 11.233 |
| 5 | 99.4 | 98.498 | −10.948 | 10.448 |
| 6 | 99.5 | 98.579 | −10.914 | 10.412 |
| 7 | 99.5 | 98.595 | −10.909 | 10.405 |
| 8 | 99.5 | 98.597 | −10.908 | 10.405 |
| 9 | 99.5 | 98.597 | −10.908 | 10.405 |
| 10 | 99.5 | 98.597 | −10.908 | 10.405 |
| 11 | 99.5 | 98.597 | −10.908 | 10.405 |
| 12 | 99.5 | 98.595 | −10.908 | 10.406 |
| 13 | 99.5 | 98.584 | −10.913 | 10.410 |
| 14 | 99.4 | 98.513 | −10.941 | 10.441 |
| 15 | 99.1 | 98.246 | −11.111 | 10.613 |

As discussed above, the present disclosure provides a method for making dimethyl ether by reactive distillation of methanol in a single piece of equipment, the reactive distillation tower 1. It requires two pieces of equipment, a reactor and a dimethyl ether separation and purification device in the prior art. That is, a reactor is combined with a distillation tower. Since catalyst is used to cause the chemical reaction, it can be called the "catalytic distillation." The pressure in the reactive distillation can be as low as 8 bars to make the dimethyl ether by dehydrating the methanol according to the present disclosure. Compared with the prior art, the equipment is smaller and less expensive, and the conversion ratio of the methanol is high, and the consumption of energy is low according to the present disclosure. Therefore, the production of the dimethyl ether is less expensive and more environmentally friendly than the prior art.

The present disclosure has been described via the detailed illustration of the preferred embodiment. Those skilled in the art can derive variations from the preferred embodiment without departing from the scope of the present disclosure. Therefore, the preferred embodiment shall not limit the scope of the present disclosure defined in the claims.

What is claimed is:

1. A method for making dimethyl ether by reactive distillation, the method including the steps of:

providing a reactive distillation tower with a top, a bottom, and rectification, reaction and stripping zones defined therein, wherein the top of the reactive distillation tower is retained at 25° C. to 40° C. while the bottom of the reactive distillation tower is retained at 84.6° C. to 170° C., wherein the reaction zone of the reactive distillation tower is filled with catalyst, wherein the reactive distillation tower has 20 distillation theoretical trays with the top as the first tray and the bottom as the $20^{th}$ tray, wherein the trays are spaced within the distillation tower with the first tray in a condenser, the second to fourth trays in a rectification zone, the fifth to $15^{th}$ trays in a reaction zone, the $16^{th}$ to $19^{th}$ trays in a stripping zone and the $20^{th}$ tray in a re-boiler;

retaining the pressure in the reactive distillation tower lower than 8.0 bars and introducing methanol into the reactive distillation tower between tray 7 and tray 10, so that the methanol travels from the reaction zone toward the bottom for contact with the catalyst to provide a top stream including dimethyl ether and a bottom stream including water and a remaining portion of the methanol; and collecting the dimethyl ether in the top of the reactive distillation tower, wherein the purity of the collected dimethyl ether is higher than 99%.

2. The according to claim 1, wherein each of the rectification, reaction and stripping zones includes several sieving trays located therein.

3. The according to claim 1, wherein each of the rectification, reaction and stripping zones includes an irregular inert material located therein.

4. The method according to claim 3, wherein irregular inert material is selected from the group consisting of a rasching ring, a lessing ring and a pall ring.

5. The method according to claim 1, wherein the catalyst includes at least one dehydrating solid catalyst selected from the group consisting of aluminum oxide, silicon oxide, thorium oxide, zirconium oxide, tricalcium phosphate, $ZnAl_2O_4$, $Al_2O_3$—$SiO_2$, $Al_2O_3$—$Cr_2O_3$, $Al_2O_3$—$MgO/SiO_2$, $MgO$—$Al_2O_3$, cadmium oxide, zinc oxide, ZSM-5, molecular sieve and acidic ion exchange resin.

6. The method according to claim 1, wherein the purity of the methanol is higher than 90%.

7. The method according to claim 1, wherein the reactive distillation tower further includes a condenser located on the top and a re-boiler located at the bottom, wherein the re-boiler heats and vaporizes the remaining portion of the methanol in the bottom stream so that it ascends and gets condensed by the condenser so that the remaining portion of the methanol descends and gets in contact with the catalyst again.

8. The method according to claim 1, wherein the methanol is introduced as 99% methanol and 1% water at a rate of 114 ton/hour.

9. The method according to claim 1, wherein the operating comprises maintaining a reflux ratio of about 0.18.

10. The method according to claim 1, wherein the energy consumption is reduced and the amount of pollution is reduced as compared to methods that are carried out in more than on piece of equipment.

11. The method of claim 1, further comprising collecting the unreacted methanol and repeating the process.

* * * * *